(12) United States Patent
Dalhoff et al.

(10) Patent No.: US 11,024,421 B2
(45) Date of Patent: Jun. 1, 2021

(54) METHOD FOR AUTOMATIC DETERMINATION OF AN INDIVIDUAL FUNCTION OF A DPOAE LEVEL

(71) Applicant: Eberhard-Karls-Universität Tübingen, Tübingen (DE)

(72) Inventors: Ernst Dalhoff, Rottenburg (DE); Dennis Zelle, Tübingen (DE)

(73) Assignee: EBERHARD-KARLS-UNIVERSITÄT TÜBINGEN, Tübingen (DE)

( * ) Notice: Subject to any disclaimer, the term of this patent is extended or adjusted under 35 U.S.C. 154(b) by 138 days.

(21) Appl. No.: 15/458,639

(22) Filed: Mar. 14, 2017

(65) Prior Publication Data
US 2017/0332977 A1 Nov. 23, 2017

(30) Foreign Application Priority Data
Mar. 15, 2016 (DE) .......................... 102016003133.6

(51) Int. Cl.
 G16H 40/63 (2018.01)
 A61B 5/12 (2006.01)
 A61B 5/00 (2006.01)

(52) U.S. Cl.
 CPC .............. *G16H 40/63* (2018.01); *A61B 5/125* (2013.01); *A61B 5/7203* (2013.01);
 (Continued)

(58) Field of Classification Search
 CPC ... A61B 5/7275; A61B 5/7278; A61B 5/7282; A61B 5/7271; A61B 5/121; A61B 5/123;
 (Continued)

(56) References Cited

U.S. PATENT DOCUMENTS 5,885,225 A * 3/1999 Keefe .................... A61B 5/121
                                                                         600/559
2012/0059274 A1    3/2012 Zoth et al.
                                  (Continued)

FOREIGN PATENT DOCUMENTS

DE          19905743 A1      9/2000
DE          69738629 T2      5/2009
                        (Continued)

OTHER PUBLICATIONS

Buckley, Jay et al. "DPOAE level mapping for detecting noise-induced cochlear damage from short-duration music exposures", Noise and Health, vol. 17, Issue 78, Sep. 2015 (Year: 2015).*
(Continued)

*Primary Examiner* — Matthew Kremer
*Assistant Examiner* — Avery M Foley
(74) *Attorney, Agent, or Firm* — Workman Nydegger

(57) ABSTRACT

The automated determination of an individual function of a DPOAE level map with $p_{dp,f}=f(L_1, L_2)$ of human or animal hearing. The method may include reading into a main memory a model function with model parameters of a DPOAE level map, based upon a number of N DPOAE measurements of a stimulation frequency pair with respectively different level pairs in a population (p) of a population of normally hearing subjects, automatically presenting n different level pairs of a stimulation frequency pair via tone output means to an individual and detecting the corresponding DPOAE's of the individual via tone recording means, wherein at least the first level pair is predefined, iteratively adapting the model function to the measured n DPOAE's until an individual function is obtained with individual parameters of a DPOAE level map of the individual, outputting the individual function and/or its individual parameters.

19 Claims, 4 Drawing Sheets

Figure 1:
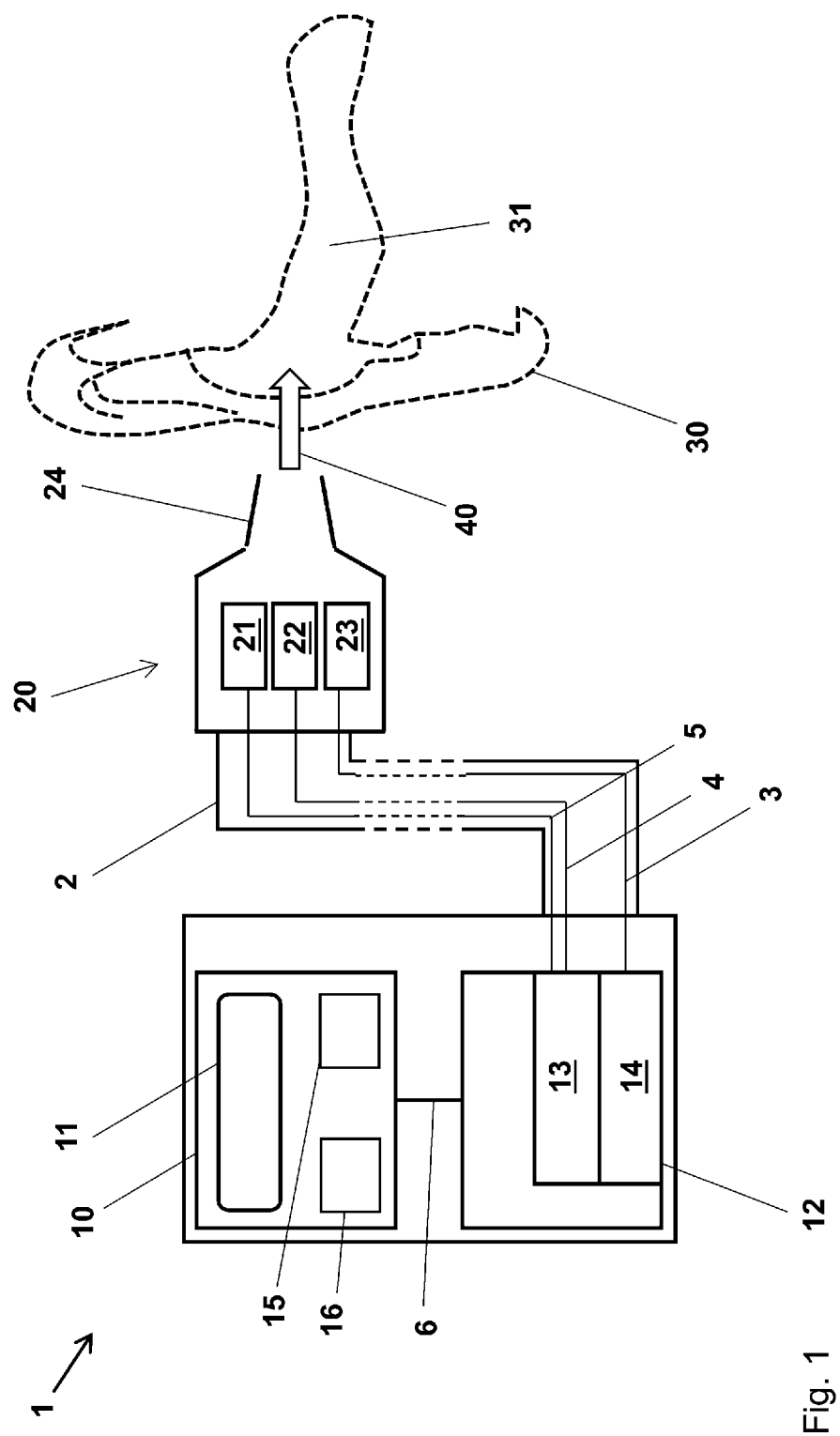

(52) U.S. Cl.
CPC .......... *A61B 5/7225* (2013.01); *A61B 5/7228* (2013.01); *A61B 5/7235* (2013.01); *A61B 5/7271* (2013.01); *A61B 5/7275* (2013.01); *A61B 5/7239* (2013.01)

(58) Field of Classification Search
CPC .. A61B 5/125; A61B 5/12; A61B 5/72; A61B 5/7203; A61B 5/7225; A61B 5/7228; A61B 5/7235; A61B 5/7239; G06F 19/00; G06F 19/34; G16H 40/63
See application file for complete search history.

(56) References Cited

U.S. PATENT DOCUMENTS

| | | | |
|---|---|---|---|
| 2014/0114209 | A1 | 4/2014 | Lodwig |
| 2016/0183849 | A1* | 6/2016 | Rembrand ............... A61B 5/16 600/559 |

FOREIGN PATENT DOCUMENTS

| | | | |
|---|---|---|---|
| DE | 102011121686 A1 | 6/2013 | |
| EP | 1027863 A1 | 8/2000 | |
| EP | 2053877 A1 | 4/2009 | |

OTHER PUBLICATIONS

Mills, David M. et al: "Interpretation of distortion product otoacoustic emission measurements", The Journal of the Acoustical Society of America 102, 413 (1997).

Whitehead, M.L.: "Dependence of distortion-product otoacoustic emissions on primary levels in normal and impaired ears. II. Asymmetry in L1, L2-space", The Journal of the Acoustical Society of America 97, 2359 (1995).

Zelle, Dennis, et al: "Level dependence of the nonlinear-distortion component of distortion-product otoacoustic emissions in humans", J. Acoustic Soc. Am. 138 (6), Dec. 2015.

Dalhoff E. et al, Two-source interference as the major reason for auditory-threshold estimation error based on DPOAE input-output functions in normal-hearing subjects, Hear Res. Feb. 2013;296:67-82. doi: 10.1016/j.heares.2012.12.003. Epub Dec. 23, 2012.

Dalhoff, et al: "Schall und Geschwindigkeits—DPOAE; Technologie, Methodik und Perspektiven", HNO; Deutsche Gesellschaft für Hals-Nasen-Ohren-Heilkunde, DE, Bd. 58, Nr. 6, 2010, Seiten 543-555.

Dennis Zelle, et al: "Extraction of otoacoustic distortion product sources using pulse basis functions", The Journal of the Acoustical Society of America, 2013, Seite EL64-EL69.

Dhar Sumitrajit, et al: "The effect of stimulus-frequency ratio on distortion product otoacoustic emission components", The Journal of the Acoustical Society of America, Bd. 117, 2005, Seiten 3766-3776.

Salata, et al: "Distortion-product otoacoustic emissions hearing-screening in high-risk newborns", Otolaryngology and head and neck surgery, US, Bd. 118, 1998, Seiten 37-43.

Whitehead M. L., et al: "Measurement of otoacoustic emissions for hearing assessment", IEEE Engineering in medicine and biology magazine, IEEE Service Center, Bd. 13, Nr. 2, 1994, Seiten 210-226.

* cited by examiner

METHOD FOR AUTOMATIC DETERMINATION OF AN INDIVIDUAL FUNCTION OF A DPOAE LEVEL

The present invention relates to a method for automatically determining an individual function of a DPOAE level map of human or animal hearing according to claim 1, as well as a system for performing this method according to the independent claim. The present invention relates in particular to a method with individual features of claim 1, as well as a method with individual features of the independent claim.

The hearing system can be understood as a chain of sequential signal processing blocks. These are traversed before the more complex perception of hearing occurs in the cortex. The first blocks of the signal processing chain are the outer ear (auricle and acoustic meatus), the middle ear (auditory ossicles with the base plate as boundary to the fluids of the inner ear), and the fluid-filled inner ear. Most hearing impairments develop in the inner ear. This includes presbyacusis which, on average from 60-70 years of age, leads to a 25 dB hearing loss in women and 35 dB hearing loss in men at frequencies of 4 kHz and higher. This is dominated by an impairment of the so-called cochlear amplifier which, in a healthy state, amplifies incoming sound waves by a factor of 300-1000, before they are converted by the inner hair cells and their synapses into neural signals.

Since about 1980, the existence of the cochlear amplifier has been successively demonstrated, with the discovery of otoacoustic emissions (OAE) by David T. Kemp playing a central role. These are tones that are generated by the active amplifier as a byproduct and are transmitted by the middle ear backwards to the acoustic meatus. These tones can be measured there with sensitive miniature microphones.

One form of OAE are distortion product otoacoustic emissions (DPOAE's), in which normally two primary tones are presented with frequencies $f_1$ and $f_2$ at levels $L_1$ and $L_2$. The nonlinear characteristic of the mechano-electric transduction of the ion channels of the outer hair cells, which generally represent the primary motor element of the cochlear amplifier in humans and mammals, yields numerous distortion products. The most easily measurable distortion product, which is therefore preferred in diagnostic applications, is the one at $f_{dp}=2f_1-f_2$, with $f_2>f_1$ and an optimum frequency ratio of about $f_2/f_1=1.2$. Currently, DPOAE's are normally excited so that both stimulation frequencies lead to highly equivalent oscillation amplitudes of the basilar membrane at the cochlear generation site of the second primary tone; accordingly, diagnostic inferences are drawn from DPOAE findings at the frequency of, and corresponding to the stimulation level of, the second primary tone $\{f_2, L_2\}$. DPOAE measurements can, for example, be performed and interpreted at various frequencies according to the method described in DE 102014108663.

One known method for determining the hearing threshold—or, more precisely, the threshold of the cochlear amplifier of the inner ear—is based upon determining the threshold at which an emission—in particular, a distortion product otoacoustic emission (DPOAE)—is measurable—a technique that was first used in humans [B. P. Kimberley and D. A. Nelson, *J. Otolaryngol.*, 18(7): 365-369, 12 1989; D. A. Nelson and B. P. Kimberley, *J. Speech Hear. Res.*, 35(5): 1142-1159, 10 1992]. For this purpose, normally a growth function is measured, such as emissions with stimulation levels of $L_2=60$ dB SPL decreasing in 5 dB increments, until a certain SNR (signal-to-noise ratio) is no longer achieved. The stimulation level at which the required SNR is reached is then termed the DPOAE threshold.

According to Boege and Janssen [P. Boege and T. Janssen, *J. Acoust. Soc. Am.*, 111(4): 1810-1818, 04, 2002], the values of the growth function are plotted in a semi-logarithmic manner, i.e., the DPOAE's are plotted linearly as sound pressure in units of [μPa] on the vertical axis against the stimulation sound pressure of the second primary tone $L_2$ in the logarithmic unit of [dB SPL]. With so-called optimum stimulation sound pressures [P. Kummer, T. Janssen, P. Hulin, and W. Arnold. Optimal $L_1$-$L_2$ primary tone level separation remains independent of test frequency in humans. *Hear. Res.*, 146(1-2): 47-56, 08 2000], typically, a linear growth function is obtained that can be extrapolated to the x-axis using linear regression. In this case, the extrapolated intersection between the growth function and the horizontal axis is termed the estimated DPOAE threshold (also, the "estimated distortion product threshold," or EDPT).

In general, this DPOAE threshold correlates well with psychoacoustically measured thresholds [P. Boege and T. Janssen, *J. Acoust. Soc. Am.*, 111(4): 1810-1818, 04, 2002, M. P. Gorga et al., *Acoust. Soc. Am.*, 113(6): 3275-3284, 06, 2003]; however, it manifests an unsatisfactorily high standard deviation and, in individual cases, a deviation of up to 40 dB [N. Schmuziger et al., *J. Acoust. Soc. Am.*, 119(4): 1937-1939, 04, 2006]. This is partly because measuring errors arise through interference from both source inputs that lead to so-called DPOAE fine structures in the measurement of conventional continuous DPOAE's, and, with extrapolation methods, this can cause serious mis-estimations [E. Dalhoff, A. Vetesnik, D. Turcanu, and A. W. Gummer. Schall-und Geschwindigkeits-DPOAE: Technologie, Methodik and Perspektiven (Sound and velocity DPOAE: Technology, methodology, and perspectives)]. *HNO*, 58(6): 543-555, 06 2010]. In order to separate the two interfering source inputs, different methods can be used, including those of pulsed DPOAE's [D. Zelle, A. W. Gummer, and E. Dalhoff. Extraction of otoacoustic distortion product sources using pulse basis functions. *J. Acoust. Soc. Am.*, 134(1): EL64-EL69, 07 2013]. Another cause of mis-estimation is that the optimum stimulation level varies individually.

Investigations by the applicant using pulsed DPOAE's have revealed that the optimum parameters for the stimulation level in a study population vary significantly on a case-by-case basis from the individual optimum stimulation parameters, with the following undesirable side effects: 1) DPOAE's with significantly lower amplitudes are measured which, with automated measuring procedures with routine designs, means that longer measuring is required to achieve the necessary SNR; 2) the global optimal stimulation path (global optimal: the determined group average) is such that it significantly distorts the growth function in individual cases and thus causes a mis-estimation in the extrapolation based upon the assumption of a linear function.

The aim of the present invention is to provide an improved method over the prior art which takes into account the individual parameters of human or animal hearing system. Ease of use is also desirable.

This aim is achieved with a method for the automated determination of an individual function of a DPOAE map card with $p_{dp,I}=f(L_1,L_2)$ of human or animal hearing that comprises the following steps:

reading into a working memory of a computer unit a model function $p_{dp,M}=f(L_1, L_2)$ with model parameters of a DPOAE map card based upon a number of N DPOAE measurements of a stimulation frequency pair $\{f_1, f_2\}$ with respectively different level pairs $\{L_1^{(1 \cdots N)}, L_2^{(1 \cdots N)}\}$ in a population (p) of normally hearing subjects, wherein $N \geq 40$ and $p \geq 2$, automatically presenting n different level pairs $\{L_1^{(1 \cdots n)}, L_2^{(1 \cdots n)}\}$ of a stimulation frequency pair $\{f_1, f_2\}$ via tone output means to an individual, and detecting the corresponding DPOAE's of the individual via tone recording means, wherein at least the first level pair $\{L_1^{(1)}, L_2^{(1)}\}$ is predefined, and wherein $n \ll N$, iteratively adapting the model function $p_{dp,M} = f(L_1, L_2)$ to the measured n DPOAE's until an individual function $p_{dp,I} = f(L_1, L_2)$ is obtained with individual parameters of a DPOAE level map of the individual by the computer unit, and outputting the individual function $p_{dp,I} = f(L_1, L_2)$ and/or its individual parameters to an output unit of the computer unit.

The method according to the invention can be used for conventional, i.e., more-or-less continuously measured, DPOAE's. Preferably, it is combined with a method that suppresses the artifacts arising from the interference of two different source inputs of a DPOAE, such as a method with pulsed DPOAE according to DE 102014108663 A1.

By means of the method according to the invention for automatically determining an individual function of a DPOAE level map, errors are avoided in the extrapolation of the growth functions that arise, as a matter of principle, in the method for measuring the distortion product threshold according to the above-described prior art.

Moreover, in comparison to the known method, more data are obtained, which are then available for diagnosis. In addition to the distortion product threshold $L_{edpt}$ and the slope of the growth function, data on the frequency resolution, compression of the underlying traveling waves, and the sound conduction loss are also detected with the method according to the invention. The general advantage of the new method is that four pieces of information, instead of two as in the prior art, are obtained from the measuring points over the same, or even less, time, and estimation errors are reduced using the previously acquired parameters (the distortion product threshold $L_{edpt}$ and the slope of the growth function).

In an advantageous embodiment of the invention, the first level pair $\{L_1^{(1)}, L_2^{(1)}\}$ has a level $L_1$ of $67 \pm 10$ dB and a level $L_2$ of $57 \pm 10$ dB. These levels of $L_1$ and $L_2$ have proven to be particularly favorable initial levels. In normally hearing subjects, these stimulation levels are still within the range up to which the level map rises more-or-less linearly; even with hearing loss up to approximately 40 dB, a DPOAE can still be measured at these levels. In most cases, values are acquired that are valid for the detection of the level map.

The model function defines a linearly rising ridge, to which linearly linked $\{L_1^{(G)}, L_2^{(G)}\}$ levels are assigned (where "G" is the index for "assigned to the ridge"). In an advantageous development of the invention, at least one-half of the measured level pairs $\{L_1^{(i)}, L_2^{(i)}\}$ lie at least 5 dB to either side of the level pair $\{L_1^{(G)}, L_2^{(G)}\}$ assigned to the ridge (where "i" is the index of the measurement from 1 to n).

In another advantageous embodiment of the invention, the different level pairs $\{L_1^{(i)}, L_2^{(i)}\}$ are presented in a sequence that is identical for each individual. With this highly simplified and uniform (rigid) method, the approximation of the individual function of a level map is slightly less precise; however, this method is very fast to perform.

It can, moreover, be advantageous when the predefined different level pairs $\{L_1, L_2\}$ are presented in a sequence that has a number of k subsequences whose level pairs $\{L_1, L_2\}$ are essentially transverse to the linearly linked level pairs $\{L_1^{(G)}, L_2^{(G)}\}$ assigned to the ridge. By incorporating the subsequences, the ridge can be sampled at several points, which increases the precision in determining the individual function of the DPOAE level map.

In a useful embodiment of the invention, $n \geq 5$ and $\leq 12$, and preferably, $6 \leq n \leq 8$. Due to the small number of provided measurements, a short measuring time is achieved, at the same time as the individual function of the DPOAE level map is effectively acquired.

Advantageously, the number of subsequences k is $\geq 2$ and $\leq 5$, which yields an effective sampling of the ridge of the DPOAE level maps.

It is also advantageous when the level pair $\{L_1^{(2 \cdots n_k)}, L_2^{(2 \cdots n_k)}\}$ of a subsequence following a first predefined level pair $\{L_1^{(1)}, L_2^{(1)}\}$ is determined with $n_k$ measurements by a function $\{L_1^{(i)}, L_2^{(i)}\} = \{L_1^{(i-1)} + \mu \cdot \Delta L_1, L_2^{(i-1)} + \mu \cdot \Delta L_2\}$ from the preceding level pair $L_1^{(i-1)}, L_2^{(i-1)}$, wherein $\mu = \pm 1$—in particular, +1—and $\Delta L_1, \Delta L_2$ is a level difference of two sequential level pairs, and has values of $\Delta L_1 = 4$ to 14 dB—preferably, from 6 to 10 dB—and $\Delta L_2 = 0$ to $-2.78$ dB—preferably, $\Delta L_2 = -1.52$ to $-2.78$ dB. The factor $\mu$ establishes the search direction (toward smaller or larger $L_1$ measuring levels) transverse to the ridge.

In a favorable advancement of the method, when the first level pair $\{L_1^{(1)}, L_2^{(1)}\}$ and the second level pair $\{L_1^{(2)}, L_2^{(2)}\}$ produce two DPOAE's with $p_{dp,I}^{(1 \cdots 2)}$ that each have a signal-to-noise ratio of $\geq 4$ dB—preferably, $\geq 10$ dB—the level of a subsequent third level pair $\{L_1^{(3)}, L_2^{(3)}\}$ is adjusted to differ by at least $\Delta L_1 \geq 4$ dB from the level of the preceding level pair $\{L_1^{(2)}, L_2^{(2)}\}$ when $p_{dp,I}^{(2)} - p_{dp,I}^{(1)} > 0$; on the other hand, the level of a subsequent level pair $\{L_1^{(3)}, L_2^{(3)}\}$ is adjusted to differ by at least $\Delta L_1 \leq -4$ dB from the level of the first level pair $\{L_1^{(1)}, L_2^{(1)}\}$, when $p_{dp,I}^{(2)} - p_{dp,I}^{(1)} \leq 0$. This procedure results in at least one point being measured to the left, and one point to the right, of the ridge, and one point being measured in-between in the vicinity of the ridge.

In an advantageous advancement of the method, when the first level pair $\{L_1^{(1)}, L_2^{(1)}\}$ does not produce any DPOAE's with $p_{dp,I}^{(1)}$ that have a signal-to-noise ratio of $\geq 4$ dB—preferably $\geq 10$ dB—the same search direction is continued until either the maximum or minimum stimulation level $L_1^{(i)}$ is reached, or a group of three valid DPOAE's with $p_{dp,I}^{(i \cdots i+2)}$ was produced that have a signal-to-noise ratio of $\geq 4$ dB—preferably, $\geq 10$ dB. In contrast to a rigid method, this results in the ridge being found even when it lies far to the side of the position anticipated for a normally hearing person, as can, for example, be the case with conductive hearing loss.

In an advantageous advancement of the method, when a group of three valid DPOAE's that have a signal-to-noise ratio of $\geq 4$ dB, and preferably of $\geq 10$ dB, is not produced in the first subsequence after measuring with i stimulation pairs, another subsequence is started with a higher level pair $\{L_1^{(i+1)}, L_2^{(i+1)}\}$, wherein the start level pair for the new subsequence is set to $L_2^{(i+3)} = L_2^{(1)} + 20 \pm 10$ dB, $L_1^{(i+3)} = L_1^{(1)} + 20 \pm 10$ dB. The level is preferably limited to the maximum technically feasible or reasonable level. This maximum level can, for example, be a sound pressure of, for example, 75-85 dB SPL. With this procedure, individual level maps that strongly deviate from the average, or their function, can still be determined.

In an advantageous embodiment of the method according to the invention, after acquiring the DPOAE's of at least 3 level pairs $\{L_1^{(1 \cdots 3)}, L_2^{(1 \cdots 3)}\}$ which are preferably assigned to a subsequence, the position of the ridge $\{L_1^{(G)}, $L_2^{(G)}\}$ along the line formed by the 3 level pairs is determined from the three level pairs $\{L_1^{(1\cdots 3)}, L_2^{(1\cdots 3)}\}$, and then a fourth level pair $\{L_1^{(4)}, L_2^{(4)}\}$ is presented that lies at a predetermined distance down the ridge, wherein the group average of the ridge direction φ is used, and wherein a slope m of the linear ridge of the level map is calculated using the DPOAE's determined from the four presented level pairs $\{L_1^{(1\cdots 4)}, L_2^{(1\cdots 4)}\}$.

Preferably, when a group of three valid DPOAE's with $p_{dp,I}^{(i-2\cdots i)}$ is produced in the first or second subsequence that each have a signal-to-noise ratio of >=4 dB—preferably, >=10 dB—the level pair below the ridge $\{L_1^{(G)}, L_2^{(G)}\} = \{L_1^{(i-2)} + \varepsilon \cdot \Delta L_1, L_2^{(i-2)} + \varepsilon \cdot \Delta L_2\}$ is calculated by automatically adapting a suitable calculation function to the associated DPOAE $p_{dp,I}^{(i\cdots i-2\cdots i)}$, wherein ε is calculated such that $p_{dp,I}(L_1^{(G)}, L_2^{(G)})$ forms a maximum, and, on that basis, a fourth level pair $\{L_1^{(i+1)}, L_2^{(i+1)}\}$ is presented, with a function $\{L_1^{(i+1)}, L_2^{(i+1)}\} = \{L_1^{(i)} + \Delta L_1, L_2^{(i)} + \Delta L_2\}$, wherein $\Delta L_2 = -15 \pm 10$ dB is adjusted, and the level pair is preferably adjusted to the projection of the anticipated ridge on the L1, L2 level, i.e., adjusted with $\Delta L_1/\Delta L_2 \approx 0.51 \pm 0.15$, and wherein the slope m of the approximately linear ridge of the level map is determined using the DPOAE's calculated from the four presented level pairs $L_1^{(i-2\cdots i+1)}, L_2^{(i-2\cdots i+1)}$.

Using the calculated slope m of the linear ridge of the level map, at least two, and preferably three, additional level pairs $L_1^{(i+1\cdots i+3)}, L_2^{(i+1\cdots i+3)}$, for example, can be automatically defined whose stimulation level is formed in a subsequence, and that are calculated based upon the known position and slope of the ridge, so that it can be anticipated that valid DPOAE's will be measured within a measuring period of $t_m \leq 40$ s, for which a model function is adapted to the preferably four already valid measured DPOAE's, and then the last two or three level pairs are determined in the model function, so that the anticipated DPOAE levels preferably lie at $p_{DPI}^{(i+1\cdots i+3)}, p_{DPI}^{(i+1\cdots i+3)} \geq 10$ μPa.

Preferably, the level pairs $\{L_1^{(1-n)}, L_2^{(1-n)}\}$ are presented as pulsed, wherein each individual pulse is presented with a duration $T_D$ of 2 to 40 ms. By using such a pulsed presentation, the influence of the two source inputs of a DPOAE can be suppressed or separated.

In an advantageous development of the method, the level pairs $\{L_1^{(1\cdots n)}, L_2^{(1\cdots n)}\}$ are presented in blocks consisting of a plurality of level pairs $\{L_1^{(1\cdots n)}, L_2^{(1\cdots n)}\}$ which are presented sequentially over time in pulses, wherein level pairs $\{L_1^{(1\cdots n)}, L_2^{(1\cdots n)}\}$ that follow each other directly in time have different stimulation frequencies $\{f_2, f_1\}$. In a block, a second level pair with different frequencies $\{f_{2,2}, f_{1,2}\}$, and possibly others with $\{f_{2,m}, f_{1,m}\}$, follows a first level pair $\{f_{2,1}, f_{1,1}\}$ that is presented as pulsed, wherein the frequency ratio is always kept close to $f_{2,m}/f_{1,m} = 1.2$. A plurality of blocks with time-frequency interleaved pulse pairs can be averaged before an evaluation occurs. By means of this measure, it is possible to use the time in which the pulse response to a presentation of a frequency pair decays to measure at a different frequency, and thereby reduce the measuring time in comparison to a procedure purely sequential with regard to the desired measuring frequencies.

In one method step, the determined individual function of a DPOAE level map and its parameters are, advantageously, saved by the computer unit in a non-volatile memory. Likewise, the determined raw data can be stored by the computer unit in the non-volatile memory. The stored data can be used by the computer unit to continuously expand the data set underlying the model function of a level map.

The stated object is also achieved by a system for performing the method, wherein the system comprises: a computer unit, a working memory, a non-volatile memory for saving a model function $p_{dp,M} = f(L1, L2)$ and model parameters of the model function, at least one tone output means controlled by the computer unit for presenting tones to an individual, and at least one tone recording means connected to the computer unit for detecting DPOAE's from the ear of the individual. An advantage of the new method is that four pieces of information, instead of two as in the prior art, are obtained for the measurements over the same, or even less, time, and estimation errors are reduced using the previously acquired parameters (the distortion product threshold $L_{edpt}$ and the slope of the growth function).

It is advantageous when at least one tone output means has a speaker with a highly linear characteristic, whereby no distortion arises when two tones $f_1, f_2$ are emitted simultaneously, and one speaker is sufficient for presenting both tones.

An output means for outputting the individual function of a DPOA level map is advantageously provided, such as a display unit, monitor, display, or a printer or interface for transmitting data to an external display unit, monitor display or printer, etc., by means of which a determined individual function of a DPOAE level map of human or animal hearing and its parameters can be output by the system and made accessible to a user.

Moreover, a non-volatile memory is, advantageously, provided for saving the determined individual function of a DPOAE level map and its parameters.

Figure 2:
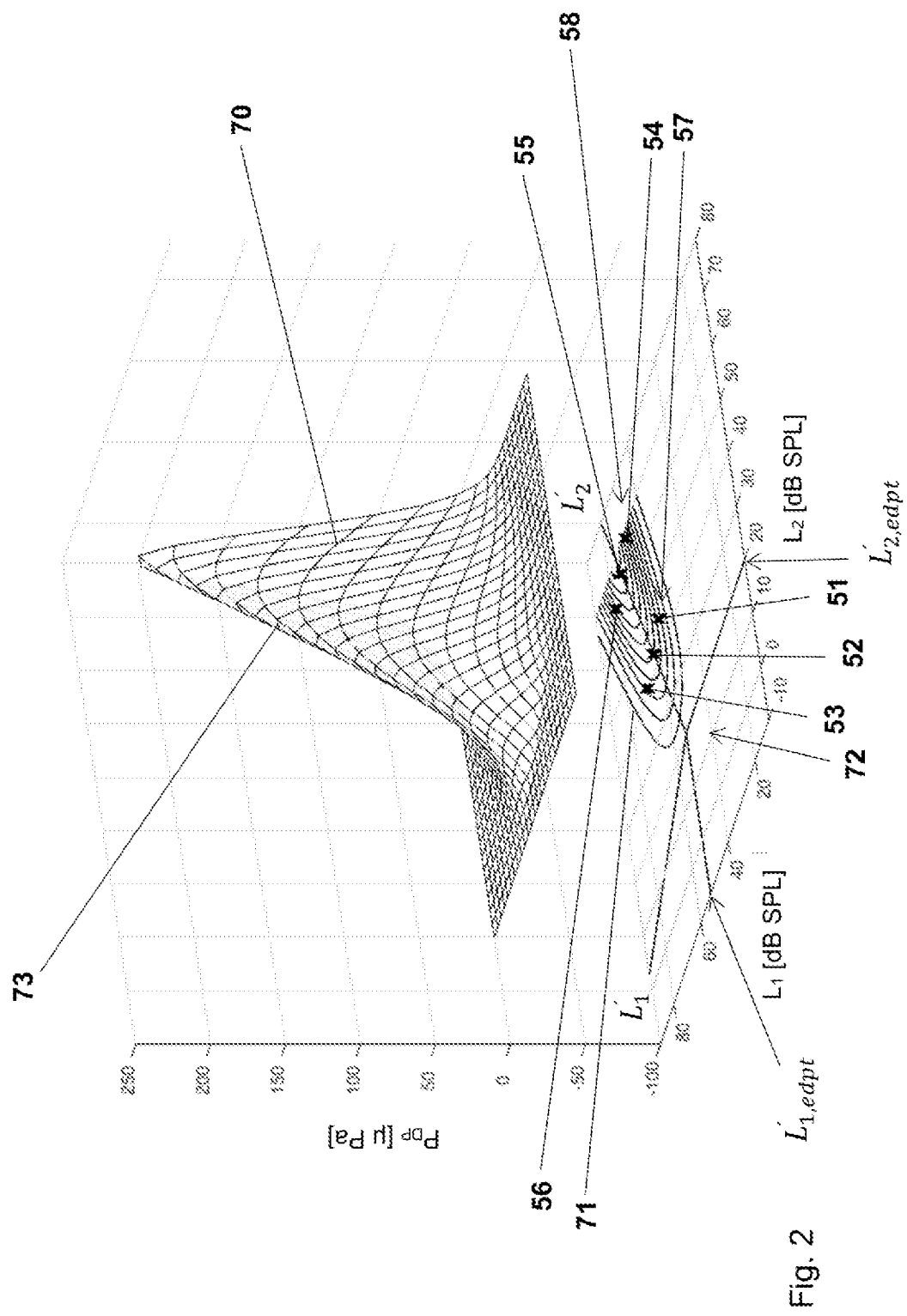
Figure 3:
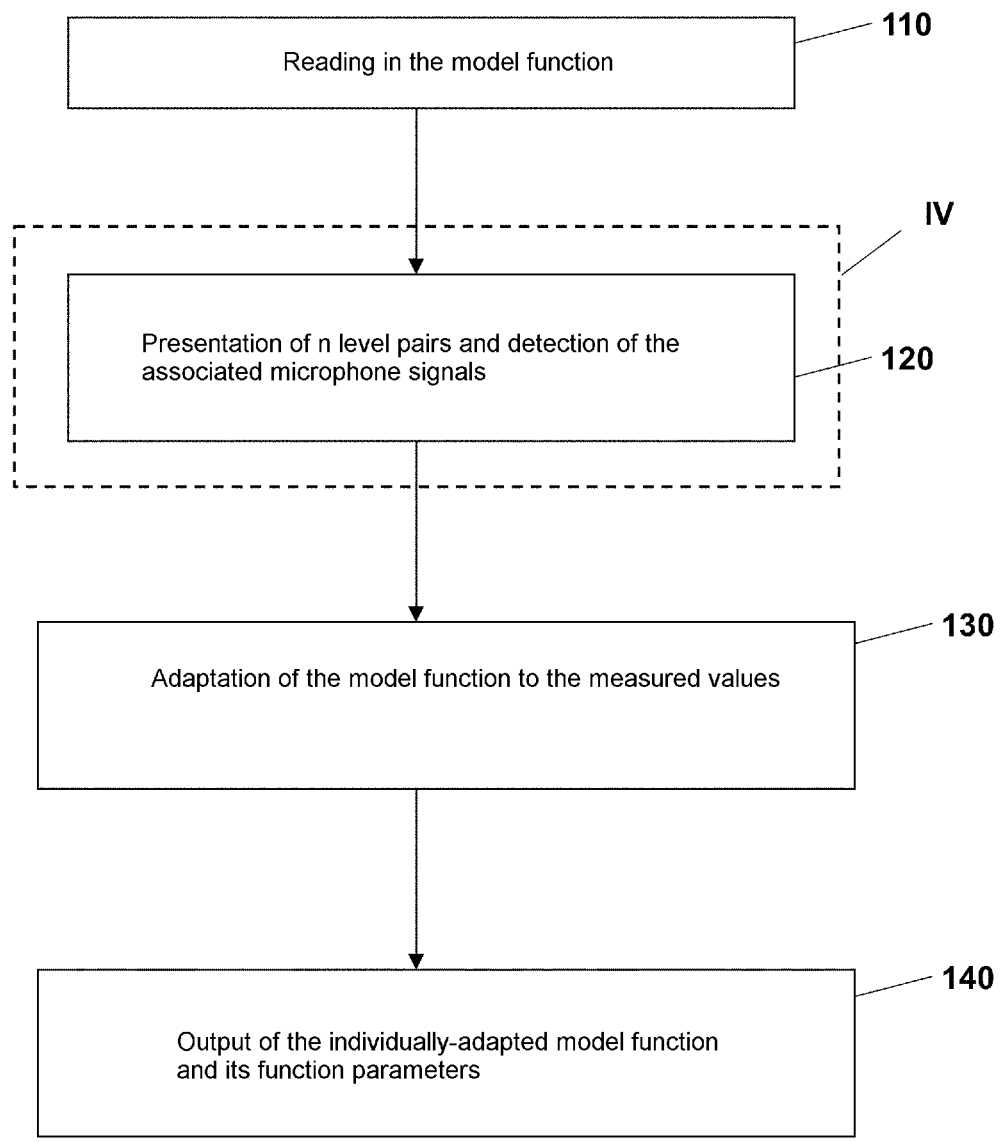
Figure 4:
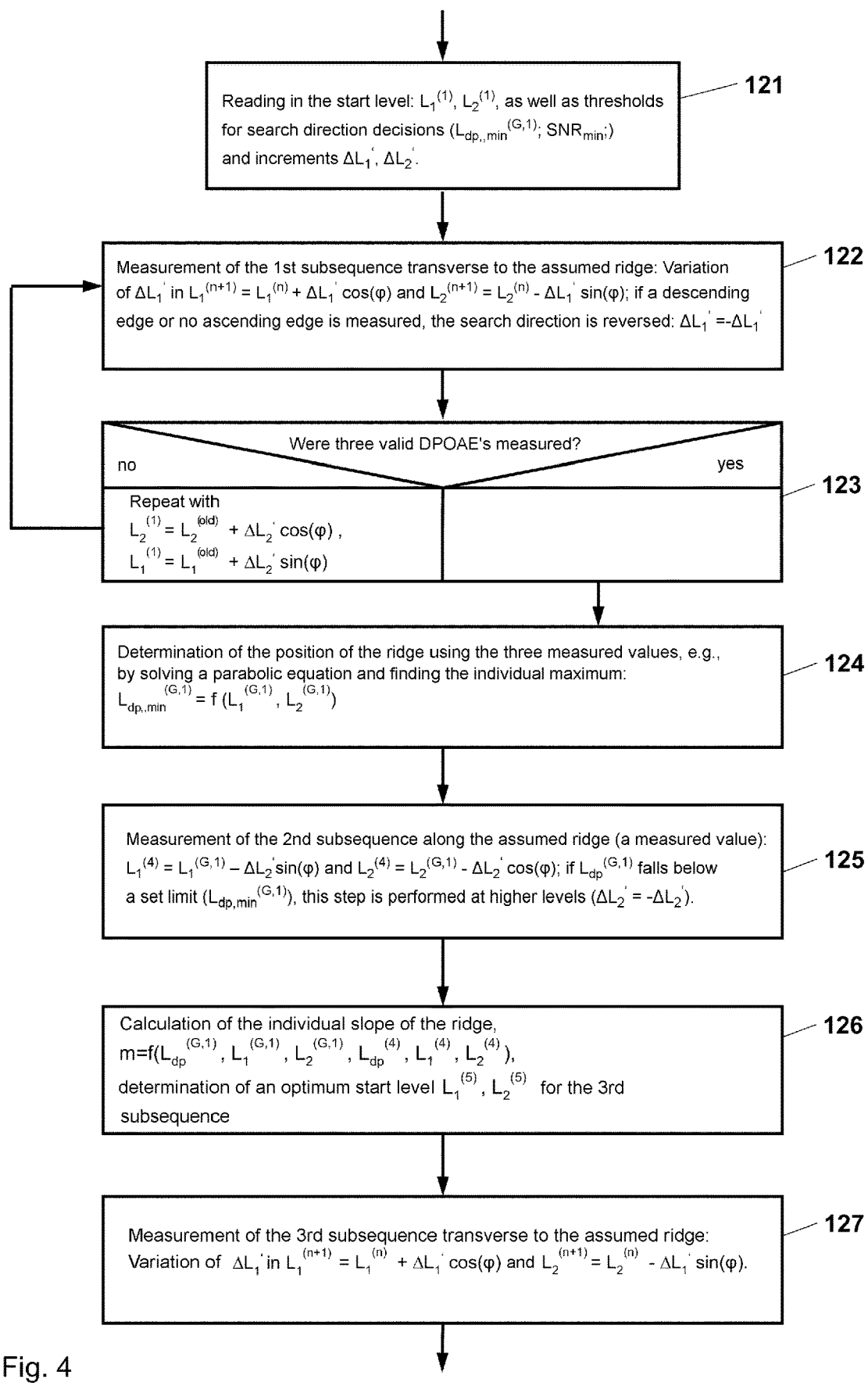

The invention will be explained in greater detail in the following figures with the help of exemplary embodiments. They show:

FIG. 1 A system for the automated determination of an individual function of a DPOAE level map;

FIG. 2 A model function whose three-dimensional graph corresponds to a model level map;

FIG. 3 Steps according to the invention of a method for the automated determination of an individual function of a DPOAE level map;

FIG. 4 Details of the method step according to marking IV in FIG. 3.

A system for the automated determination of an individual function of a DPOAE level map of human or animal hearing in one possible embodiment according to the invention is depicted in FIG. 1. A probe unit 20 that can be positioned in an ear—especially, an OAE probe—and a computer unit 10 belong to the system 1. The probe unit has a probe tip 24 which can be inserted into the acoustic meatus of an ear. Arranged in the probe unit 20 is a tone recording means 23 such as a microphone that is configured to record tones coming from the acoustic meatus. Moreover, a first and second tone output means 21 and 22 are provided in the probe unit 20 that function as f1 sound generators (tone output means 21) and as f2 sound generators (tone output means 22). The tone output means 21, 22 can be designed as speakers. In addition, only one tone output means and only one speaker may be provided, which is configured to simultaneously emit two tones $f_1, f_2$ and, in particular, possesses a highly linear characteristic. The probe unit 20 is, for example, connected by a cable connection 2 to the control unit which contains the computer unit 10. Shielded leads 3, 4, 5 are preferably provided in the cable connection 2, by means of which the tone output means 21, 22 and tone pickup means 23 are connected to an AD/DA converter unit 12 of the control unit. For its part, the AD/DA converter unit 12 is connected to a computer unit 10 by means of at least one lead 6 for a bi-directional data exchange. Alternatively to the cable connection 2, the probe unit 20 can also communicate wirelessly with the control unit or computer unit 10. The wireless connection could, for example, be a Bluetooth wireless link, or another suitable wireless connection that preferably has a short range.

The computer unit 10 has a working memory 15 and a non-volatile memory 16 in which a model function $p_{dp,M}=f(L1, L2)$ for a model level map of human or animal hearing is stored, along with the parameters belonging to this model function. Likewise, the instructions for performing the method according to the invention are saved in the non-volatile memory 16. Moreover, the system 1 has an output means 11 or a display unit such as a display, monitor, etc., by means of which a determined individual function of a DPOAE level map of human or animal hearing and its parameters are output by the system 1 and can be made accessible to a user. The output means 11 can also be realized in the form of an interface by means of which an external output device such as a printer or monitor can be connected to the system.

To perform an automated measuring procedure for generating an individual function of a DPOAE level map of human or animal hearing, the probe unit 23 is inserted in the direction of the arrow 40 into the acoustic meatus 31 of an ear 30 (indicated in FIG. 1). The method according to the invention will be explained below with reference to FIGS. 3 and 4.

Initially, however, a model function, by way of example, is depicted in FIG. 2 whose three-dimensional graph 70 corresponds to a model level map. The model function depicted as an example is based upon measuring data of $p \geq 2$—in the present case, $p=6$—normally hearing individuals with $N \geq 40$—in the present case, $N=47$—different measured level pairs $\{L_1^{(1 \cdots N)}, L_2^{(1 \cdots N)}\}$ at stimulation frequencies $f_2=2$ kHz and $f_1=1.67$ kHz. The stimulation frequencies $f2$ and $f_1$ of a level pair $\{L_1, L_2\}$ are preferably linked by a frequency ratio $f_2/f_1=1.2$. In the process, a certain distortion product was evaluated, which is preferably at the frequency $f_{dp}=2f_1-f_2$. The uppercase indices in parentheses correspond to the 1st to Nth measuring point.

The model function defines a more-or-less linearly rising ridge 73, to which more-or-less linearly linked level pairs $\{L_1^{(G)}, L_2^{(G)}\}$ are assigned. Lines transverse to the ridge can be defined by the relationship $L_2+aL_1=C$, wherein C is any constant, and wherein a is the slope parameter of the projection of the ridge onto the $\{L_1, L_2\}$ plane. In mathematical terms, the position of the ridge is defined by a sequential set of gradient vectors of the scalar field that is formed by the DPOAE's, wherein all other field lines formed by gradient vectors run toward and enter this ridge. In the $\{L_1, L_2\}$ plane 71 below the model level map, shifted for the sake of clarity by $p_{dp}=100$ μPa, the transformed $\{L'_1, L'_2\}$ coordinate system 72 is drawn that arises by shifting the origin toward $\{L_{1,edpt}, L_{2,edpt}\}$ and rotating on arctan (a), as well as height lines of the level map at 20 μPa intervals. The $L'_2$ axis corresponds to the projection of the ridge of the level map onto the $\{L_1, L_2\}$ plane. The $L'_1$ orthogonally intersects the model hill approximating the level map. This section of the hill transverse to the ridge is approximated by a second-order parabola whose spread is indicated by a parameter c, and the input is expressed in the following equation:

$$L'_{dp}=-c(L'_1)^2+L'_{dp}{}^{(G)}$$

with $$L'_{dp}{}^{(G)}=20 \log_{10}(m(L'_2))$$

$L'_{dp}$ and $L'_{dp}{}^{(G)}$ are the level of any DPOAE, or a DPOAE located on the ridge, and m is the slope of the ridge along the $L'_2$ axis.

The $\{L'_1, L'_2\}$ coordinate system is located in the area created by the known coordinate system $\{L_1, L_2\}$ of the primary tone level. The above-addressed coordinate transformation can be expressed, for example, as follows:

$$L'_1=(L_1-L_{1,edpt})\cos(\varphi)-(L_2-L_{(2,edpt)}) \sin(\varphi)$$

$$L'_2=(L_1-L_{1,edpt})\sin(\varphi)+(L_2-L_{(2,edpt)}) \cos(\varphi)$$

The projection of the ridge of the $L_{dp}$ hill corresponds to the $\{L_1, L_2\}$ plane of the $L'_2$ axis. Moreover, the point $\{L_{2,edpt}, L_{1,edpt}\}$ corresponds to the base point of the ridge of the $L_{dp}$ hill, and φ is the angle between the $L_2$ axis and the projection of the ridge of the $L_{dp}$ hill onto the $\{L_1,L_2\}$ plane, established by the aforementioned $L'_2$ axis. The angle φ is accordingly the angle at which the $L'_2$ axis is rotated relative to the $L_2$ axis. In a broader sense, the base point of the ridge can be interpreted as being equivalent, but not identical with, the "estimated distortion product level" (edpt), as is known from [P. Boege and T. Janssen., *J. Acoust. Soc. Am.,* 111(4): 1810-1818, 2002].

The model function for the level map, for the validity range of positive $L_{dp}$, can be described by five free parameters: a; b; c; $L'_{2,edpt}$; m. To calculate this surface from measured values, at least 5 DPOAE's are therefore needed.

The method according to the invention is based upon the adaptation of the three-dimensional model function to a roughly sampled three-dimensional DPOAE level map with, preferably, at least 5 measurements. In a first exemplary embodiment of the method according to the invention for the automated determination of an individual function of a DPOAE level map with $p_{dp}=f(L_1, L_2)$ of human or animal hearing, a stimulation level pair $\{L_1, L_2\}$ 51, 52, 53, 54, 55, 56 is presented to the hearing of an individual that is predefined from the system n, e.g., n=6, which can be seen in FIG. 1. These six predefined stimulation pairs $\{L_1, L_2\}$ 51, 52, 53, 54, 55, 56 are, for example, marked in FIG. 2 in the $\{L_1, L_2\}$ plane. From these 6 predefined stimulation level pairs $\{L_1, L_2\}$ 51, 52, 53, 54, 55, 56, which are presented in two subsequences 57, 58, DPOAE's are then determined which are used in the method according to the invention to determine the individual function of a DPOAE level map.

In a first step 110 of the method according to the invention according to FIG. 3, the above-described model function is first read out of the non-volatile memory 16 into the computer unit 10 of the system 1, or the working memory 15 of the computer unit 10. After the model function is read in, a number of different level pairs $\{L_1^{(1 \cdots n)}, L_2^{(1 \cdots n)}\}$ of a stimulation frequency pair $\{f_1, f_2\}$ are output by the system 1 in a second step 120 by the tone output means 21, 22 of the probe unit 20, or are presented to an individual, and the corresponding DPOAE's of the individual are detected by the tone recording means 23, wherein at least the first level pair $\{L_1^{(1)}, L_2^{(1)}\}$ is predefined, and wherein n<<N The corresponding DPOAE's are fed by the AD/DA converter unit 12 to the computer unit 10 for further processing. The uppercase indices in parentheses correspond to the 1st to nth measuring point.

In a first version of the method according to the invention, which can be termed an adaptive variant, the second step 120 contains a series of substeps 121 to 127 which will be explained in greater detail below with reference to FIG. 4.

According to FIG. 4, in a first substep 121 of the second step 120, a start level $\{L_1^{(1)}, L_2^{(1)}\}$ (preferably a level $L_1$ of 67±10 dB and a level $L_2$ of 57±10 dB) for a first level pair is read out of the non-volatile memory 16 into the computer unit 10. Moreover, in this substep 121, the increments $\Delta L_1$, $\Delta L_2$ for the additional level pairs $\{L_1^{(2\cdots n)}, L_2^{(2\cdots n)}\}$ and the thresholds for the search direction decisions $L_{dp,min}^{(G,1)}$; $SNR_{min}$ are read into the computer unit 10. $SNR_{min}$ designates the desired SNR (signal-to-noise ratio), and $L_{dp,min}^{(G,1)}$ designates the DPOAE level on the ridge that must exist at least along a first subsequence of k subsequences so that a following subsequence below the first one with a sufficient SNR can be anticipated. If this value is not achieved, then the next subsequence above the first one, i.e., up the slope, is sampled, in order to avoid excessive measuring time in achieving a sufficient SNR. The increments $\Delta L_1$, $\Delta L_2$ designate the level difference between two sequential level pairs, wherein $\Delta L_1$ has in particular a value of $\Delta L_1$=4 to 14 dB—preferably, from 6 to 10 dB—and wherein $\Delta L_2$=0 to −2.78 dB—preferably, $\Delta L_2$=−1.52 to −2.78 dB.

In a second substep 122 of the second step, the measurements of the first subsequence of k subsequences are performed transversely to the assumed ridge of the individual function of a level map. The DPOAE's are then measured at the above-described stimulation frequencies $f_2$=2 kHz and $f_1$=1.67 kHz. The stimulation frequencies $f_2$ and $f_1$ of a level pair $\{L_1, L_2\}$ are preferably linked by a frequency ratio $f_2/f_1$=1.2. The subsequence belongs to a number of k subsequences, wherein k≥2 and ≤5. In each subsequence, a number of $n_k$ level pairs $\{L_1, L_2\}$ is measured.

Corresponding to the established increments $\Delta L_1$, $\Delta L_2$, the start level $\{L_1^{(1)}, L_2^{(1)}\}$ is varied corresponding to the formula $L_1^{(n+1)} = L_1^{(n)} + \Delta L_1' \cos(\varphi)$ and the additional formula $L_2^{(n+1)} = L_2^{(n)} - \Delta L_1' \sin(\varphi)$. If a descending edge, or no ascending edge, is measured in the measured subsequence, the search direction is reversed, and $\Delta L_1' = -\Delta L_1'$.

A third substep 123 checks whether at least three valid DPOAE's have been measured. If this check is positive, i.e., three valid DPOAE's were measured, the procedure advances to the next substep 124. If three valid DPOAE's were not measured, then the measurement is repeated, in which, based upon the original stimulation level $L_1^{(old)}$, $L_2^{(old)}$, a new stimulation level $L_1^{(1)}, L_2^{(1)}$ is determined by:

$$L_2^{(1)} = L_2^{(old)} + \Delta L_2 \cos(\varphi),$$

$$L_1^{(1)} = L_1^{(old)} + \Delta L_1 \sin(\varphi).$$

In the following fourth substep 124, the position of the ridge of the individual function is determined using the three valid determined measured values, e.g., by solving a parabolic equation and finding the individual maximum according to the function:

$$L'^{(G,1)}_{dp} = f(L_1^{(1\cdots 3)}, L_2^{(1\cdots 3)})$$

Here, $L'^{(G,1)}_{dp}$ means the point on the estimated ridge of the individual model function whose associated stimulation pair lies on the line formed by $\{L_1^{(1\cdots 3)}, L_2^{(1\cdots 3)}\}$. The position of the ridge of the individual function at the higher stimulation levels $L^{(1\cdots 3)}$ is already known from substep 124; however, the slope of the ridge, i.e., the parameter m, is not known.

In the following fifth sub step 125 of the second step 120, a second subsequence is measured along the assumed ridge, wherein only one measured value is determined. The measurement is performed using the formula $L_1^{(4)} = L'^{(G,1)}_{dp} - \Delta L'_2 \sin(\varphi)$.

If $L'^{(G,1)}_{dp}$ falls below a preset limit $(L'^{(G,1)}_{dp,min})$, this step is performed on a higher level ($\Delta L_2 = -\Delta L_2$).

The value there measured of the DPOAE ($L^{(4)}_{dp}$) is then used in the sixth substep 126 to determine the individual slope of the ridge m.

In the sixth substep 126 of the second step 120, the individual slope of the ridge is calculated using the formula $m = f(L_{dp}^{(G,1)}, L_1^{(G,1)}, L_2^{(G,1)}, L_{dp}^{(4)}, L_1^{(4)}, L_2^{(4)})$. Using the calculated slope m of the ridge, a start level $L_1^{(5)}, L_2^{(5)}$ is then determined for the third subsequence.

In the seventh substep 127 of the second step 120, the measurements of the third subsequence are then performed transversely to the assumed ridge of the function: a variation of $\Delta L'_1$ in $L_1^{(n+1)} = L_1^{(n)} + \Delta L'_1 \cos(\varphi)$ is performed.

Preferably, at least one-half of the level pairs $\{L_1, L_2\}$ used in the measurements lie at least 5 dB to either side of the group of the level pairs assigned to the ridge (of the model function) $\{L_1^{(G)}, L_2^{(G)}\}$.

Using the measured values determined in the second step 120 and its substeps 121 to 127, the above-described model function is adapted to the obtained measured values in a third step 130 in the computer unit 10. In so doing, the three-dimensional model function $p_{dp,M} = f(L_1, L_2)$ is adapted to the measured DPOAE values. The adaptation is performed using the mathematical methods of equalization calculus, e.g., using the method of least squares, i.e., with the iterative minimization of the difference between n measured values and the values of the model function $p_{dp,M} = f(L_1, L_2)$ for the measured n DPOAE's (corresponding to the associated $L_1, L_2$ coordinates) until an individual function $p_{dp,I} = f(L_1, L_2)$ is obtained by the computer unit 10 with individual parameters of a DPOAE function and level map of the individual. Accordingly, an individual function/level map of the hearing of an individual is thereby quickly obtained with much less measuring effort.

In a fourth step 140, the individually adapted function and its function parameters are output on output means 11 of the system 1, such as a display, monitor, printer, etc. The output function parameters contain, in particular, the above-described parameters a; b; c; $L'_{2,edpt}$, and the slope of the ridge m. As mentioned, the output means 11 can also be realized in the form of an interface by means of which an external output device such as a printer or monitor can be connected to the system 1.

In a possible additional method step, the determined individual function of a DPOAE level map and its parameters are, advantageously, saved by the computer unit 10 in the non-volatile memory 16. Likewise, the measured raw data of the computer unit 10 can be stored in non-volatile memory 16. The stored data can be used by the computer unit 10 to, for example, continuously expand the data set underlying the model function of a level map.

The following information can be gleaned from the individually adapted function and the associated function parameters obtained according to the invention:

An approximated distortion product threshold can be calculated that provides information on the threshold of the input signal for the inner hair cells of the measured hearing. $L_{2,edpt}$ can be considered a corresponding parameter.

The width of the ridge, described in the function by the parameter c, is a measure of the compression, and thus of the frequency resolution of the underlying traveling waves in the measured hearing.

The position and the angle expressed in the function by the parameters a; b contains information on the nature of a hearing loss: In the event of a pure conductive loss, the angle (expressed in the function by the parameter a) does not change; instead, the hill shifts in a first approximation to the same extent toward a higher $L_1$ and $L_2$ level. When, for example, the shift of the hill (relative to standard values, or relative to a reference measurement of the individual at an earlier time) coincides with the degradation of the distortion product threshold, i.e., $\Delta L_2 \approx \Delta L_1 \approx \Delta L_{2,edpt}$, a pure conductive loss can be assumed.

The slope of the ridge expressed by the parameter m provides information about a potential conductive loss. As long as the hearing loss lies below 30 dB, it can be assumed that the slope corresponds to standard values in the event of a pure conductive loss, whereas, when there is a deviation from the standard value, a proportional reduction of the retrograde middle ear transmission at $f_{dp}$ is indicated.

In an alternative variant of the method according to the invention, instead of substeps 121 to 127 during the measurements in the second step 120, a number of n determined or predefined, but different, level pairs $\{L_1, L_2\}$ (where n is preferably ≥5 and ≤12—in particular, ≥5 and ≤8) is output by the system, and the reaction of the hearing of an individual to these level pairs $\{L_1, L_2\}$ is detected. This version can be termed a rigid method. The level pairs $\{L_1, L_2\}$ can, in turn, be measured in a number of k subsequences (57, 58; cf. FIG. 2), wherein k≥2 and ≤12. The n level pairs are then largely static, and there is no adaptation of the second and possibly third subsequence to the results of the measurements in the first subsequence, as is the case in the above-described method. The number n level pairs $\{L_1, L_2\}$ is determined based upon a consideration of the measuring time (the fewest possible measuring points) relative to the achievable precision (the most possible measuring points). In this rigid method with predetermined stimulation levels, $L'_1=0\pm6$ dB can always be measured, e.g., with $L'_2=40$ dB for the three higher stimulation levels, and $L'_2=25$ dB for the three lower stimulation levels, and within a group of three stimulation levels. In the $\{L_1, L_2\}$ coordinate system, this would correspond to the excitation levels $L_2$=68.1; 65.6; 63.1; 42.8; 45.3; 40.3 and $L_1$=68.0; 73.5; 79.0; 63.3; 57.8; 68.7 (cf. FIG. 2). The aim of the choice of $L'_1=0\pm6$ dB is to measure the position of the ridge with three points that are transverse to the assumed position of the ridge: given $f_2=2$ kHz, the DPOAE with $\Delta L'_1 \pm 6$ dB typically decreases to approximately 50% of the maximum value. If, primarily, individuals with normal hearing are to be measured, as is usually the case in screening tests, the fixed arrangement will provide favorable results. Exceptions must, however, also be discerned. This is feasible using the root mean square error in the model adaptation. If the error is too high, i.e., the rms error (rms: root mean square) is, for example, greater than 5 μPa, additional level pairs must be measured until the error is sufficiently low.

Additional $\Delta L'_1$ steps are recommended in this case. The same procedure is required when individual measuring points cannot be recorded because the signal-to-noise ratio is too low.

In conclusion, it should be noted that, in contrast to the employed and above-described frequency ratio $f_2/f_1$ of 1.2, another frequency ratio can be chosen. Accordingly, the frequency ratio $f_2/f_1$ can, for example, be set at a different suitable value between 1.15 and 1.35. Moreover, the frequency ratio $f_2/f_1$ could be a function of f2.

LIST OF REFERENCE NUMBERS

1 System
2 Cable connection
3 First line
4 Second line
5 Third line
6 Fourth line
10 Computer unit
11 Output means
12 AD/DA converter unit
13 DA converter
14 AD converter
15 Main memory
16 Non-volatile memory with a saved model function
20 Probe unit, OAE probe
21 First tone output means, f1 sound generator
22 Second tone output means, f2 sound generator
23 Tone recording means, microphone
24 Probe tip
30 Ear
31 Acoustic meatus
40 Arrow
51 Stimulation level pair $\{L_1, L_2\}$
52 Stimulation level pair $\{L_1, L_2\}$
53 Stimulation level pair $\{L_1, L_2\}$
54 Stimulation level pair $\{L_1, L_2\}$
55 Stimulation level pair $\{L_1, L_2\}$
56 Stimulation level pair $\{L_1, L_2\}$
57 First subsequence
58 Second/additional subsequence
70 Graph/model level map
71 $\{L_1, L_2\}$ plane
72 Transformed $\{L'_1, L'_2\}$ coordinate system
73 Ridge (of the DPOAE model level map)
110 First method step
120 Second method step
121 First substep
122 Second substep
123 Third substep
124 Fourth sub step
125 Fifth substep
126 Sixth substep
127 Seventh substep
130 Third method step
140 Fourth method step

The invention claimed is:

1. A method for automated determination of an individual function of a distortion product otoacoustic emission (DPOAE) level map with $p_{dp,I}=f(L_1, L_2)$ of human or animal hearing, characterized in that the method comprises the following steps:

reading into a main memory of a computer unit a model function $p_{dp,M}=f(L_1, L_2)$ with model parameters of a DPOAE level map for a human or animal hearing, based upon a number of N DPOAE measurements of a stimulation frequency pair $f_1$, $f_2$ with respectively different level pairs $\{L_1^{(1\cdots N)}, L_2^{(1\cdots N)}\}$ in a population (p) of normally hearing subjects, wherein N≥40 and p≥2, wherein the model function $p_{dp,M}=f(L_1, L_2)$ provides a function representing a DPOAE level map corresponding to the population (p) of normally hearing subjects, determining n DPOAEs for an individual by automatically presenting n different level pairs $\{L_1^{(1\cdots n)}, L_2^{(1\cdots n)}\}$ of the stimulation frequency pair $f_1$, $f_2$ via tone output means to the individual and, for each different level pair $\{L_1^{(1\cdots n)}, L_2^{(1\cdots n)}\}$, detecting a corresponding DPOAE of the individual via tone recording means, wherein at least the first level pair $\{L_1^{(1)}, L_2^{(1)}\}$ is predefined, and wherein n<<N, iteratively adapting the model function $p_{dp,M}=f(L_1, L_2)$ to the measured n DPOAE's until the individual function $p_{dp,I}=(L_1, L_2)$ is obtained with individual parameters of a DPOAE level map of the individual by the computer unit, the iteratively adapting comprising iteratively minimizing a difference between the n measured DPOAEs and values given by the model function $p_{dp,M}=f(L_1, L_2)$ for the corresponding each different level pair $\{L_1^{(1\cdots n)}, L_2^{(1\cdots n)}\}$, and outputting the individual function $p_{dp,I}=f(L_1, L_2)$ and/or its individual parameters to an output means of the computer unit.

2. The method according to claim 1, characterized in that the first level pair $\{L_1^{(1)}, L_2^{(1)}\}$ has a level $L_1^{(1)}$ of 67±10 dB and a level $L_2^{(1)}$ of 57±10 dB.

3. The method according to claim 1, characterized in that the model function has a more or less linearly rising ridge to which more or less linearly linked level pairs $\{L_1^{(G)}, L_2^{(G)}\}$ are assigned, wherein at least one-half of the measured level pairs $\{L_1, L_2\}$ lie at least 5 dB to either side of a group of the level pairs $\{L_1^{(G)}, L_2^{(G)}\}$ assigned to the ridge (73).

4. The method according to claim 1, characterized in that the different level pairs $\{L_1, L_2\}$ are presented in a sequence that is identical for each individual.

5. The method according to claim 1, characterized in that the predefined, different level pairs $\{L_1, L_2\}$ are presented in a sequence that has a number of k subsequences whose level pairs $\{L_1, L_2\}$ are essentially transverse to linearly linked level pairs $\{L_1^{(G)}, L_2^{(G)}\}$ assigned to a ridge.

6. The method according to claim 1, characterized in that n is ≥5 and ≤12 or n is ≥5 and ≤8.

7. The method according to claim 5, characterized in that k≥2 and ≤8.

8. The method according to claim 5, characterized in that a level pair $\{L_1^{(2\cdots nk)}, L_2^{(2\cdots nk)}\}$ of a subsequence following the first predefined level pair $\{L_1^{(1)}, L_2^{(1)}\}$ is determined with $n_k$ measurements by a function $\{L_1^{(i)}, L_2^{(i)}\}=\{L_1^{(i-1)}+\mu\cdot\Delta L_1, L_2^{(i-1)}+\mu\cdot\Delta L_2\}$ from the respectively preceding level pair $\{L_1^{(i-1)}, L_2^{(i-1)}\}$, wherein $\mu=\pm 1$ and $\Delta L_1, \Delta L_2$ is a level difference of two sequential level pairs and has values of $\Delta L_1=4$ to 14 dB and $\Delta L_2=0$ to -2.78 dB.

9. The method according to claim 1, characterized in that, when the first level pair $\{L_1^{(1)}, L_2^{(1)}\}$ and the second level pair $\{L_1^{(2)}, L_2^{(2)}\}$ produce two DPOAE's with $p_{dp,I}^{(12)}$ that each have a signal-to-noise ratio of >=4 dB, the level of a subsequent third level pair $\{L_1^{(3)}, L_2^{(3)}\}$ is adjusted to differ by at least $\Delta L_1 \geq 4$ dB from the level of the preceding second level pair $\{L_1^{(2)}, L_2^{(2)}\}$ when $p_{dp,I}^{(2)}-p_{dp,I}^{(1)}>0$; on the other hand, the level of the subsequent third level pair $\{L_1^{(3)}, L_2^{(3)}\}$ is adjusted to differ by at least $\Delta L_1 \leq -4$ dB from the level of the first level pair $\{L_1^{(1)}, L_2^{(1)}\}$, when $p_{dp,I}^{(2)}-p_{dp,I}^{(1)} \leq 0$.

10. The method according to claim 1, characterized in that, when the first level pair $\{L_1^{(1)}, L_2^{(1)}\}$ does not produce any DPOAE's with $p_{dp,I}^{(1)}$ that have a signal-to-noise ratio of ≥4 dB, the same search direction is continued until either a maximum or minimum stimulation level $L_1^{(i)}$ is reached, or a group of three valid DPOAE's with $p_{dp,I}^{(i\cdots i+2)}$ was produced that have the signal-to-noise ratio of ≥4 dB.

11. The method according to claim 1, characterized in that, when a group of three valid DPOAE's that have a signal-to-noise ratio of ≥4 dB, is not produced in a first subsequence, another subsequence is started with a higher level pair $\{L_1^{(i+1)}, L_2^{(i+1)}\}$, wherein a start level pair for the new subsequence is set to $L_2^{(i+3)}=L_2^{(1)}+20\pm10$ dB, $L_1^{(i+3)}=L_1^{(1)}+20\pm10$ dB, or at most to a maximum achievable level.

12. The method according to claim 1, characterized in that, after acquiring the DPOAE's of at least 3 level pairs $\{L_1^{(1\cdots 3)}, L_2^{(1\cdots 3)}\}$, the position of the ridge $\{L_1^{(G)}, L_2^{(G)}\}$ along a line formed by the three level pairs is determined from these three level pairs $\{L_1^{(1\cdots 3)}, L_2^{(1\cdots 3)}\}$, and a fourth level pair $\{L_1^{(4)}, L_2^{(4)}\}$ is presented that is placed at a predetermined distance down the ridge, wherein a group average of a ridge direction φ is used, and wherein a slope of the linear ridge of the level map is calculated using the DPOAE's determined from the four presented level pairs $\{L_1^{(1\cdots 4)}, L_2^{(1\cdots 4)}\}$.

13. The method according to claim 1, characterized in that, when a group of three valid DPOAE's with $p_{DP,I}^{i-2\cdots i}$ is produced in a first or second subsequence that each have a signal-to-noise ratio of >=4 dB, a level pair below the ridge $\{L_1^{(G)}, L_2^{(G)}\}=\{L_1^{(i-2)}+\varepsilon\cdot\Delta L_1, L_2^{(i-2)}+\varepsilon\cdot\Delta L_2\}$ is calculated by adapting a mathematical function to an associated DPOAE $p_{DP,I}^{i-2\cdots i}$, wherein ε must be calculated so that $p_{DP,I}(L_1^{(G)}, L_2^{(G)})$ forms a maximum, and on that basis a fourth level pair $L_1^{(i+1)}, L_2^{(i+1)}$ is presented, with a function $\{L_1^{(i+1)}, L_2^{(i+1)}\}=\{L_1^{(i)}+\Delta L_1, L_2^{(i)}+\Delta L_2\}$, wherein $\Delta L_2=-15\pm10$ dB is adjusted, and the level pair is adjusted to a projection of an anticipated ridge on the $L_1, L_2$ level, adjusted with $\Delta L_1/\Delta L_2=0.51\pm0.15$, and wherein a slope m of an approximately linear ridge of the level map is determined using the DPOAE calculated from the four presented level pairs $L_1^{(i-2\cdots i+1)}, L_2^{(i-2\cdots i+1)}$.

14. The method according to claim 1, characterized in that the level pairs $\{L_1^{(1\cdots n)}, L_2^{(1\cdots n)}\}$ are presented as pulsed, wherein each individual pulse is presented with a duration $T_D$ of 2 to 40 ms.

15. The method according to claim 14, characterized in that the level pairs $\{L_1^{(1\cdots n)}, L_2^{(1\cdots n)}\}$ are presented within a measuring block consisting of a plurality of level pairs $\{L_1^{(1\cdots n,m)}, L_2^{(1\cdots n,m)}\}$ which are presented sequentially over time in pulses, wherein level pairs $\{L_1^{(1\cdots n,i)}, L_2^{(1\cdots n,i)}\}$; $\{L_1^{(1\cdots n,i+1)}, L_2^{(1\cdots n,i+1)}\}$ that follow each other directly in time have different stimulation frequencies $\{f_{2,i}, f_{1,i}\}$; $\{f_{2,i+1}, f_{1,i+1}\}$.

16. The method according to claim 15, characterized in that, in an additional method step, the determined individual function of the DPOAE level map and its parameters are saved by the computer unit in a non-volatile memory.

17. A system for performing the method according to claim 1, the system comprising a computer unit, the computer unit configured to carry out the reading, determining, iteratively adapting, and outputting steps, a main memory, and a non-volatile memory for storing the model function $p_{dp,M}=f(L_1, L_2)$ and the model parameters of the model function, the tone output means controlled by the computer unit for presenting tones to the individual, with the tone recording means connected to the computer unit for detecting DPOAE's from the ear of the individual.

18. The system according to claim 17, characterized in that the tone output means is a speaker with a highly linear characteristic.

19. The system according to claim 17, characterized in that the output means is provided for outputting the individual function of the DPOAE level map to a user.

* * * * *